US009694059B2

(12) United States Patent
Salazar Onfray et al.

(10) Patent No.: US 9,694,059 B2
(45) Date of Patent: Jul. 4, 2017

(54) EX VIVO, FAST AND EFFICIENT PROCESS TO OBTAIN ACTIVATED ANTIGEN-PRESENTING CELLS THAT ARE USEFUL FOR THERAPIES AGAINST CANCER AND IMMUNE SYSTEM-RELATED DISEASES

(71) Applicants: UNIVERSIDAD DE CHILE, Santiago (CL); ONCOBIOMED, Santiago (CL)

(72) Inventors: Flavio Andres Salazar Onfray, Santiago (CL); Mercedes Natalia Lopez Nitsche, Santiago (CL); Cristian Javier Pereda Ramos, Santiago (CL); Raquel Elvira Aguilera Insunza, Santiago (CL); Alejandro Felipe Escobar Alvarez, Santiago (CL)

(73) Assignee: Universidad de Chile, Santiago (CL)

( * ) Notice: Subject to any disclaimer, the term of this patent is extended or adjusted under 35 U.S.C. 154(b) by 0 days.

(21) Appl. No.: 13/875,119

(22) Filed: May 1, 2013

(65) Prior Publication Data
US 2014/0072596 A1    Mar. 13, 2014

Related U.S. Application Data

(63) Continuation-in-part of application No. 12/680,709, filed as application No. PCT/EP2008/062909 on Sep. 26, 2008, now abandoned.

(30) Foreign Application Priority Data

Sep. 28, 2007   (CL) .................................. 2825/2007

(51) Int. Cl.
| | |
|---|---|
| *C12N 5/00* | (2006.01) |
| *C12N 5/02* | (2006.01) |
| *A61K 39/00* | (2006.01) |
| *C12N 5/0784* | (2010.01) |
| *C12N 5/09* | (2010.01) |
| *A61K 35/12* | (2015.01) |

(52) U.S. Cl.
CPC ........ *A61K 39/0011* (2013.01); *C12N 5/0639* (2013.01); *C12N 5/0693* (2013.01); *A61K 2035/124* (2013.01); *A61K 2039/5154* (2013.01); *A61K 2039/55511* (2013.01); *C12N 2500/84* (2013.01); *C12N 2501/02* (2013.01); *C12N 2501/05* (2013.01); *C12N 2501/056* (2013.01); *C12N 2501/07* (2013.01); *C12N 2501/22* (2013.01); *C12N 2501/23* (2013.01); *C12N 2501/24* (2013.01); *C12N 2501/25* (2013.01); *C12N 2506/11* (2013.01)

(58) Field of Classification Search
None
See application file for complete search history.

(56) References Cited

U.S. PATENT DOCUMENTS

| | | |
|---|---|---|
| 2002/0155108 A1 | 10/2002 | Barbera-Guillem |
| 2006/0140983 A1 | 6/2006 | Paulucka et al. |
| 2007/0014795 A1 | 1/2007 | Dhodapkar et al. |

FOREIGN PATENT DOCUMENTS

| | | |
|---|---|---|
| EP | 1254953 | 11/2002 |
| JP | 2000143534 | 5/2000 |
| JP | 2000357242 | 12/2000 |
| WO | 9703186 | 1/1997 |
| WO | 02053176 | 7/2002 |
| WO | 2004018659 | 3/2004 |
| WO | 2004050855 | 6/2004 |

OTHER PUBLICATIONS

Reyes et al., 2013, Br. J. Canc. vol. 109: 1488-1497.*
Caputo et al., 2011, Cell Cycle, vol. 10: 2924-36.*
Aguilera et al., 2011, Clin. Can. Res. vol. 17: 2474-83.*
Schadendorf et al., 1996, British J. Can. vol. 74: 194-199.*
Wong et al., 1997, J. Biol. Chem. vol. 272: 28779-28785.*
Hoal-Van Helden et al., 1986, Br. J. Canc. vol. 54: 287-295.*
Fearnley, D.B., et al., "Monitoring Human Blood Dendritic Cell Numbers in Normal Individuals and in Stem Cell Transplantation", Blood, 1999 vol. 93, pp. 728-736, American Society of Hematology.
Banchereau, J. et al., "Dendritic Cells Controllers of the Immune System and a New Promise of Immunotherapy," Annals New York Academy of Sciences, 2003, pp. 180-187, vol. 987, New York Academy of Sciences.
Moser M., et al., "Dendritic cell regulation of Th1-Th2 development" Nature Immunology, Sep. 2000, vol. 1, No. 3, pp. 199-205, Nature America Inc.
Mellman, I., et al., "Dendritic Cells: Specialized and Regulated Antigen Processing Machines", Cell, 2001, vol. 106, pp. 255-258, Cell Press.
Delmarre, L., et al., "Presentation of Exogenous Antigens on Major Histocompatibility Complex (MHC) Class I and MHC Class II Molecules is Differently Regulated During Dendritic Cell Maturation," The Journal of Experimental Medicine, Jul. 7, 2003, vol. 198, No. 1, pp. 111-122, The Rockefeller University Press.
Sallusto, F., et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor," Journal of Experimental Medicine, Apr. 1994, vol. 179, pp. 1109-1118, The Rockefeller University Press.
Svane, I.G., et al., "Clinical application of dendritic cells in cancer vaccination therapy," APMIS, 2003, vol. 111, pp. 818-834, Denmark.

(Continued)

*Primary Examiner* — Amy Juedes
(74) *Attorney, Agent, or Firm* — Bryan Cave LLP

(57) ABSTRACT

The present invention relates to an ex vivo, fast and efficient process to obtain activated antigen-presenting cells that are useful for therapies against cancer and immune system-related diseases. At the same time, it is related to a cellular composition that contributes to stimulate the activated antigen-presenting cells to induce a specific immune response against tumors in patients with cancer or other pathologies involving immune responses.

26 Claims, 12 Drawing Sheets

(56) References Cited

OTHER PUBLICATIONS

Dauer, M., et al., "Mature Dendritic Cells Derived from Human Monocytes Within 48 Hours: A Novel Strategy for Dendritic Cell Differentiation from Blood Precursors," The Journal of Immunology, 2003, vol. 170, pp. 4069-4076, The American Association of Immunologists, Inc.

Palucka, K.A., et al., "Dendritic Cells as the Terminal Stage of Monocyte Differentiation," The Journal of Immunology, 1998, vol. 160, pp. 4587-4595, The American Association of Immunologists, Inc.

Steinman, R.M., et al., "The Induction of Tolerance by Dendritic Cells That Have Captured Apoptotic Cells," Journal of Experimental Medicine, Feb. 2000, vol. 191, No. 3, pp. 411-416, The Rockefeller University Press.

Lopez, M., et al., "Advances in cellular immunotherapy for malignant melanoma," Rev Med Chile, 2004; vol. 132; pp. 1115-1126.

Escobar, A., et al., "Dendritic cell immunizations alone or combined with low doses of interleukin-2 induce specific immune responses in melanoma patients," Clinical and Experimental Immunology, 2005; vol. 142, pp. 558-568, British Society of Immunology.

Nestle, F.O., et al., "Vaccination of melanoma patients with peptide- or tumor lysate-pulsed dendritic cells," Nature Medicine, Mar. 9198, vol. 4, No. 3, pp. 328-332, Nature Publishing Group.

Randolph, G.J., et al., "Differentiation of Monocytes into Dendritic Cells in a Model of Transendothelial Trafficking," Science, 1998, vol. 282, pp. 480-483, The American Association for the Advancement of Science.

Vegh, Z., et al., "Generation of tumor cell lysate-loaded dendritic cells preprogrammed for IL-12 production and augmented T cell response," Cancer Immunology Immunotherapy, vol. 52, No. 2, Feb. 2003 (Feb. 2003), pp. 67-79, XP002545927, ISSN: 0340-7004, table 1.

International Search Report & Written Opinion issued Oct. 2, 2009 in Application No. PCT/EP2008/062909.

Dauer, et al., 2005, FastDC Derived from Human Monocytes With 48 H effectively prime tumor antigen-specific cytotoxic T cells,: Journal of Immunological Methods, vol. 302: 145-155.

Qui, et al., Jan. 2006, "Heat-Shocked tumor cell lysate-pulsed dendritic cells induce effective anti-tumor immune response in-vivo," World Journal of Gastroenterology., vol. 21: 473-478.

Feurestein, et al., 2000, "A method for the production of cryopreserved aliquots of antigen-preloaded, mature dendritic cells ready for clinical use," Journal of Immunolgical Methods, vol. 245: 15-29.

Herr, et al., 2000, "Mature dendritic cells pulsed with freeze-thaw cell lysates define an effective in vitro vaccine designed to elicit EBV-specific CD4+ and CD8+ T lymphocyte responses," Blood, vol. 96: 1857-64.

* cited by examiner

FIGURE 1

| | Amount of PBMCs obtained from Leukapheresis | Amount of PBMC cultured per volume of medium (20 ml) | Amount of cells obtained per volume of medium (20 ml) | % purity (CD11c+) | Amount of DCs obtained per volume of medium (20 ml) | % efficiency | Minimal number of vaccines obtained per volume (10 X $10^6$/dosis) |
|---|---|---|---|---|---|---|---|
| Standard DC | 5–10 X $10^9$ | 2.5 X $10^8$ | 1.8 X $10^6$ | 85–90 % | 1.5–1.6 x $10^6$ | 0.64 | 3 |
| Rapid DC | 5–10 X $10^9$ | 2.5 X $10^8$ | 6 x $10^6$ | 70–80 % | 4.2–4.8 x$10^6$ | 1.92 | 12 |

FIGURE 2

MELANOMA ASSOCIATED ANTIGENS PRESENT IN CELL LINES OF THE LYSATE (TRIMEL)

| Cell lines | MelanA Mart 1 (#) | gp-100 (*) | MC1R (#) | MCSP (#) | S100 (*,#) | HER2/neu (#) | MAGE-1 (S) | MAGE-3 (S) |
|---|---|---|---|---|---|---|---|---|
| Mel 1 | + | + | + | + | + | + | + | − |
| Mel 2 | + | + | + | + | + | − | − | + |
| Mel 3 | + | + | + | + | + | + | − | + |

Immunocytochemistry (*), Flow cytometry (#), RT-PCR (S).

FIGURE 12

| Patient's code | Diagnosis | *Side effects | Stable disease (months) | Progression (months) | DTH |
|---|---|---|---|---|---|
| 42 MT | Colorectal Cancer | 1 | 16 | No | 6 mm (+) |
| 43 MT | Melanoma | 1 | 33 | No | 18 mm (+) |
| 44 MT | Lung cancer | No | 0 | 4 | NR |
| 45 MT | Melanoma | 1 | 5 | 2 | 5 mm (+) |
| 46 MT | Melanoma | No | 7 | 2 | 8 mm (+) |
| 47 MT | Ovarian cancer | No | 0 | 2 | 3 mm (−) |
| 48 MT | Melanoma | 1 | 0 | 4 | 0 mm (−) |
| 49 MT | Prostate cancer | 1 | 7 | No | 5 mm (+) |
| 50 MT | Melanoma | 1 | 6 | No | 8 mm (+) |
| 51 MT | Melanoma | 1 | 2 | 2 | 7 mm (+) |
| 2 MT | Lung cancer | No | 2 | No | ongoing |
| 53 MT | Melanoma | No | 2 | No | ongoing |
| 54 MT | Melanoma | No | 0 | 3 | ongoing |
| 55 MT | Melanoma | No | 1 | No | ongoing |

* Side effects= (No) No side effects. (1) Minor, (2) moderate, do not require medication, (3) moderate and require medication. (4) Severe.

EX VIVO, FAST AND EFFICIENT PROCESS TO OBTAIN ACTIVATED ANTIGEN-PRESENTING CELLS THAT ARE USEFUL FOR THERAPIES AGAINST CANCER AND IMMUNE SYSTEM-RELATED DISEASES

CROSS-REFERENCE TO RELATED APPLICATIONS

This application is a continuation-in-part of U.S. patent application Ser. No. 12/680,709 filed on Aug. 18, 2010, which is a national stage application under 371 of International Application No. PCT/EP2008/062909 filed on Sep. 26, 2008, which claims priority to Chilean Patent Application No. 2825/2007 filed on Sep. 28, 2007, all of which are incorporated herein by reference. Pertinent cell lines were deposited at the International Depository Authority of Canada (IDAC), at 1015 Arlington Street, Winnipeg, Canada R3E 3R2, on Sep. 26, 2016. This IDAC deposit includes: accession number 260916-01 of cell line "Mel 1" herein, accession number 260916-02 of cell line "Mel 2" herein, and accession number 260916-03 of cell line "Mel 3" herein.

FIELD OF INVENTION

This invention refers to an ex vivo, fast and efficient process to obtain activated antigen-presenting cells that are useful for therapies against cancer and immune system-related diseases. At the same time, it is related to a cellular composition that contributes to stimulate the activated antigen-presenting cells to induce a specific immune response against tumors in patients with cancer or other pathologies involving immune responses.

STATE OF THE ART

With the improvement of new medical technologies and the upgrading of material conditions, life expectancy for world population has increased, especially in developed countries. This has lead to an increase incidence of various tumors and cancer in the population, showing an overall augmented number of patients suffering from cancer, as well as immune system-associated disorders Cancer is a pathology in which cells with an uncontrolled capacity for growth and spreading are able to invade their originating organs or tissues and spread towards the body through the blood or lymphatic tissues. Its aberrant expansion destroys healthy tissues, producing metabolic unbalances and altering the function of organs, many times causing death. In the light of recent developments, the treatment for this disease has been improved. However, this pathology still remains one of the primary causes of death worldwide.

Over the last thirty years, great progress has been achieved in understanding the contribution of the immune system, regarding tumor cell recognition and destruction, so the manipulation of the immune system as an antitumoral tool has become a potential alternative for cancer treatment. The so-called antitumoral immune therapy may be used as a complement for usual treatments of oncological conditions, such as surgery, chemotherapy and radiotherapy.

Although some types of immune therapy are already a part of the usual treatment of some types of cancer, there are others in a preclinical or clinical trial stage. Among the strategies employed in immune therapy, the use of immune molecules, such as interferons, interleukins, colony-stimulating factors and monoclonal antibodies has been of vital importance. A different strategy is the active immunization against tumors, which is commonly known as cancer vaccines.

Therapeutic vaccines for cancer disorders are a form of specific immune therapy, whose purpose is stimulating or strengthening a direct response of the patient against the tumor through immunization, for instance with inactivated or radiation exposed tumor cells, or by administering tumor antigen-containing (Ag) vaccines.

Tumor-associated antigens or tumor-specific antigens are protein-origin molecules mainly, which are differentially expressed in the tumor and normal tissue, where they become a target for immunological responses.

Cancer vaccines are generally provided after the onset of the disease; to this effect complete attenuated cells may be used, as well as cellular compounds or specific antigens with the purpose of stimulating the patient's immune system. These vaccines may be commonly classified as complete tumor cell vaccines or vaccination preparations from tumor antigens. The former may be divided in complete autologous cell vaccines coming from the subject itself and in complete allogeneic cells consisting in a combination of tumor cells of the same histological type but from different patients. These preparations are manufactured in laboratory facilities and they are usually combined with adjuvant.

The tumor-associated Ags can be obtained from complete tumor cells, from tumor-purified proteins or peptides, from artificially synthesized peptide sequences or genetic material obtained of the tumors.

In regard to this, vaccines of specific proteins/peptides are designed from tumor-associated antigens, which are recognized by T lymphocytes. The antigenic peptide or protein may be administered purified or synthesized as a part of the vaccine composition or by inducing the synthesis of the tumor peptide or antigen into the target cell by transfection.

To introduce genetic material into the body, viral vectors, such as adenoviruses may be used. Although, adenovirus is the most commonly used virus, retroviruses have also been used with successful results. These viral vectors might also encode additional cytokine genes beside the tumor-associated antigen.

The DNA vaccines consisting in plasmids coding tumor Ag have the advantage of acting independently from the subject's MHC haplotype. New strategies are currently being developed for this kind of vaccines involving the fusion of genes, such as coding agents for idiotypic determinants of the immunoglobulin molecule with a sequence of the titanic toxoid antigen, which enables the activation of the immune system's effector mechanisms.

Another therapeutic alternative corresponds to the dendritic cell vaccines or professional antigen-presenting cells (APC), which is a technique recently incorporated to clinical practice and seems to be interestingly effective for generating a specific CTL response against tumors and infectious agents.

Notwithstanding the multiplicity of developing alternatives for the treatment of tumors, the success of active immunotherapy in cancer treatment may be affected by multiple factors such as the heterogeneity existing among tumor cells, for instance, the low immunogenicity of tumor antigens and the immune evasion mechanisms developed by tumors to avoid the immunological response. The tumor-associated antigens—potentially immunogenic molecules—may be effective targets for cancer vaccines, but they may also be present in normal cells and not be recognized by the immunological system for different reasons, such as the cryptic expression due to the physical orientation or configuration of Ag on the cell surface, the physical separation, the separation by cell membranes or masking by other cell components; lower antigenic expression than the required for immune recognition or a different surface distribution regarding tumor cells.

Recently, the existence of regulatory lymphocytes (Treg) has been described. Tregs are able to inhibit immune responses and their main role is keeping tolerance in order to avoid autoimmune responses. There is evidence that these cells may exert a deleterious effect on the generation of antitumoral responses in patients with cancer, which would enhance the tumor growth.

Consequently, objectives pursued by the active immune therapy against cancer would be: overcoming the immune suppression produced by tumor-deriving factors, increasing the immunogenicity of antigens that may help eliminating tumors and metastasis and the clinical recovery of patients when treated with any antitumoral vaccine.

The development of dendritic cell (DC) vaccines is an explored alternative with promissory results. The DCs are originated in the bone marrow from pluripotential progenitors and about 0.5% of total blood mononuclear cells correspond to DC in circulation and they are very hard to maintain in culture conditions (Fearnley D. B. et al. 1999). DCs are a subgroup of leukocytes with a great antigen-presentation capacity and the potential to induce and regulate the immune response (Svane I M et al. 2003, Banchereau J et al. 2003). DCs have proven to be the most effective antigen-presenting cells (APC); this is why they are called professional APCs. By presenting intra- and extra-cellular antigens, they are able to induce a T lymphocyte CD4* and CD8*-mediated specific immune response. DCs are strategically positioned in peripheral tissues in possible antigen-entering areas, where they are able to capture process and present them associated with histocompatibility molecules (HCM). DCs comprise a heterogeneous population with different surface markers (phenotype) associated with their maturation tempo. It is thought that different stimuli would be able to trigger qualitatively different maturation processes, thus suggesting that DCs could interpret environment signals, which depend on the stimulus nature and then develop to mature DCs which are able to polarize a the LT immune response into Th1 or Th2 (cellular or humoral immune response respectively) or to a tolerogenic type of response (Moser M and Murphy K M. 2000). During the maturing transition, the phenotype of DCs changes, cytoplasmatic prolongations increase as well as the characteristic markers of immature DCs (DCi) decrease; at the same time the expression of co-stimulating molecules begin to increase, such as CD40, CD80 and CD86, CD83, class I and II MHC molecules and the chemokine receptor CCR-7, which recognizes chemokines CCL19 and CCL21, which guide migration of DCs to the T zone of secondary lymphoid organs, where the naive antigen-specific LT clone may be found (Mellman I et al. 2001, Delamarre L et al. 2003).

Since obtaining these cells from peripheral blood is difficult and laborious intense, different methods have been developed during the last decade for their in vitro generation from monocytes, thus allowing a greater quantity of DCs to be available for study and use in immune therapies as an alternative treatment for cancer. During the last two decades, different clinical trials of vaccination with autologous DCs have been published in relation to the treatment of advanced cancer. In most of them researchers use DCs generated from CD14+ monocytes or CD34+ progenitor cells cultured for seven to ten days in a culture medium supplemented with granulocytes and macrophages colony of stimulating factors (GM-CSF) and interleukine-4 (IL-4), adding the alpha tumor necrosis factor (TNF-$\alpha$) as a maturing stimulus (Sallusto F. et al. 1994, Svane I G. et al. 2003). It has been proposed, however, that generating mature in vitro DCs is possible in shorter periods. FASTDC are obtained in 48 hours, using a combination of proinflammatory factors as IL-6, IL-1$\beta$, prostaglandin E2 and TNF-$\alpha$ (Dauer et al. 2003) as maturing stimulus. Three days (3 days APC) are generated by mixing of macrophages and Langerhans cells obtained by a combination of GM-CSF and TNF-$\alpha$ described in the international application WO2004/050855. Although these protocols shorten the DC-production times, their drawbacks are the high cost derived from the use of human recombinant cytokines, further necessary addition of antigens able to arouse immunological responses against tumors and in some cases, the lower levels of DCs maturing capacity, which limits their clinical use due to the potential risk of tumor evasion or tolerance induction.

Other recent studies state that several population of DC on the periphery derives from monocytes that infiltrate tissues due to inflammatory stimuli probably mediated by innate immunity (Palucka K A et al. 1998). This differentiation process of in vivo monocytes is performed in early stages of the immunological response in order to allow in less than a week, an effective T lymphocyte mediated response (Gwendalyn J. et al. 1998). The current DC production methods involve in vitro incubation periods of several days, which lessens the strength, viability and quality of DCs or use a complex set of pro-inflammatory recombinant factors that generate a type of APC that is questioned for some of its phenotypic features associated with activated monocytes, immature DCs and macrophages; this is why its therapeutic use against infections or tumors is limited due to possibility of tolerance induction (J Immunol. 2004, Dauer M, et al. 2003). There is evidence in literature that activated monocytes and immature DCs have the capacity to react to stimulus from molecules termed pathogen-associated molecular patterns, PAMPs, through pattern recognitions receptors, PRRs (Steinman R M et al. 2006). There are several PRRs ligands and they exist not only in pathogens, but as endogenous molecules expressed mainly in transformed, infected or stressed cells and are able to activate PRRs.

Among the experiences developed to obtain antigen-loaded DCs, the method described in US20020155108 consists in an ex vivo DC co-culture performed along with soluble antigens, without physical contact, an antibody is included against the soluble antigen in order to form immune complexes which the DCs are able to absorb, process and present on the cell surface.

In the Japanese patent application JP2000143534, a method is disclosed to obtain DC vaccines with antigen-presenting activity. The mentioned method consists in incubating a DC with antigen-presenting activity with the following components: a suspension of cells containing a DC cellular precursor, for instance bone marrow cells, blood cells from umbilical cord or peripheral blood monocytes; a differentiation-inducing agent, for instance combinations of GM-CSF, IL-4, TNF-$\alpha$, stem cells factor and TNF-$\alpha$; and a chemokine.

In addition, WO02053176 describes a method to produce autologous APCs loaded with a mixture of at least two lysate of allogeneic melanoma tumor cells. Maturation of DC is induced with TNF, E2 prostaglandin and/or polyribocytidilic acid.

The US 2007/0014795 describes in turn a method for activation of antigen presenting cells, which might be DCs.

In published results from Lopez M: et al (Rev Med Chile 2004; 132: 1115-1126) and Escobar et al. (Clin. Exp. Immunology 2005; 142(3): 555-568) the authors demonstrate a procedure for DCs production from monocytes by 7-day incubation and a later incubation with TNF-α and with tumor lysate of three lines of allogeneic melanoma. In addition, Nestle F O et al. (Nature Medicine N 4, 328-332 (1998) discloses a clinical study where DCs are induced by monocyte culture for also during seven days with GM-CSF, IL-4 and a lysate of tumor cells or a group of known peptides identified through recognition by T cytotoxic lymphocytes.

The state of the art allows us identify some weaknesses and limitations resulting in drawbacks for the development and practical application of the technology disclosed in those inventions. On one hand, the methods described require a laborious and time consuming preparation of these cells, up to 8 to 9 days in total. Moreover, these technologies result in the aging of cells, which may shorten their survival in the body after their injection or may affect their functionality. In addition to the above, these technologies also involve a slow differentiation of cells which does not reflect a natural process, since it is known that monocytes differentiating in vivo into DCs are able to do it in hours and not within 3 or more days (Randolph G J, Science 1998).

From the methodological point of view, the methods described in the art provide both operating disadvantages and inefficiencies as compared with this invention. First, classic DCs require a longer in vitro incubation time (7-9 days) which increases the production cost, increasing the use of reagents acting as differentiation factors and culture media, in addition to an increased risk of infection or cell's death. Second, in the processes described in the state of the art, the rate of DCs obtained from blood mononuclear cells (PBMC) is at least three times lower than the obtained by using the method proposed in this invention. In addition, the APCs obtained according to this invention have characteristics that make them more effective to be used as anti-tumor therapy in patients with cancer.

Consequently, in order to optimize the in vitro generation of APCs, this invention refers to an extract or lysate of tumor tissue or cells and to a fast an effective method to produce APCs, from pre activated peripheral blood monocytes by differentiation cytokines and matured with components of cell lysate of tumor tissue. Lysate obtained through our treatment have a double function: on one hand, they are able to induce differentiation and maturation of activated monocytes into APCs highly similar to mature DCs and they are also able to provide a wide range of tumor antigens able to induce the activation of T lymphocytes with the potential to recognize and destroy tumor cells.

DESCRIPTION OF FIGURES

The figures described below are proposed in order to show background information to back-up and describe the invention; therefore, they are not intended to restrict and must by no means be understood as limiting the scope of the development proposed.

FIG. 1 corresponds to a table showing a comparative evaluation of the efficiency between the method proposed herein of rapid differentiation of dendritic cells (Rapid DC) as compared with the traditional method of seven-day DC production (DC standard). It is noted that from the same number of peripheral blood cells (PBMC), nearly 4 times the quantity of DCs is obtained when using the method proposed in this invention, which in turn allows obtaining a greater quantity of doses for vaccination of patients. Also, the use of fewer differentiation factors and culture medium, the facility and cost of production is reduced to half of the value.

FIG. 2 shows the expression of melanoma-associated antigens expressed in some lines of melanoma used to obtain an extract or lysate of tumor cells comprising part of the invention. The expression of melanoma-associated antigens was determined by Immunohistochemistry (*), flow cytometry (#) or RT-PCR (§). The combination of these lines altogether is able to express a wide range of melanoma antigens.

Figure 8:
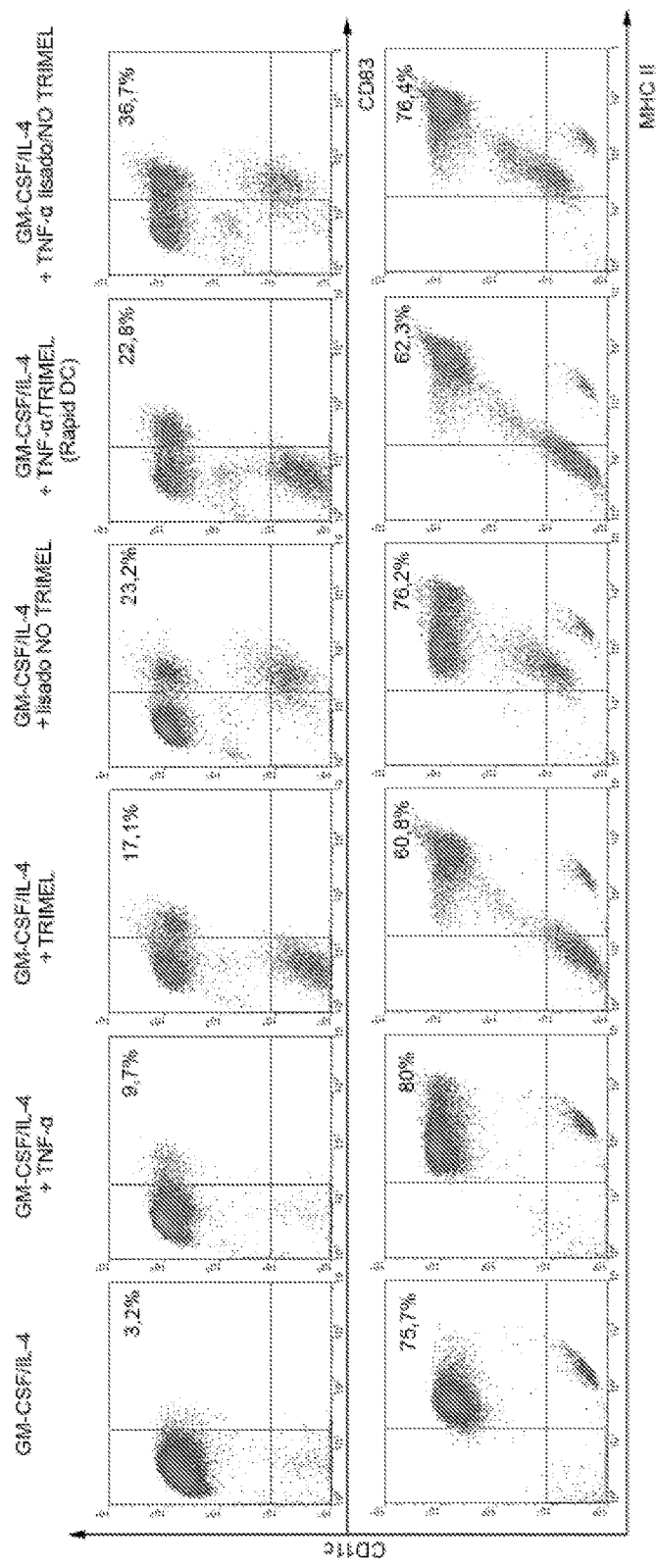

FIG. 8 shows that tumor lysate other than TRIMEL, made of other three melanoma cell lines is also able to induce Rapid DC maturation process. A tumor lysate called NO TRIMEL lysate was prepared from 3 cell lines, FM 55 (skin melanoma), OCM-1 and OCM-3 (eye melanoma) and the maturation inducing effect was evaluated on monocytes. The expression of CD11c, CD83 and MHC II markers was determined by flow cytometry. Levels of maturation markers are similar to those obtained using TRIMEL. This result indicates that the combination of different melanoma lysate obtained from different individuals is able to induce the maturation process of monocytes into mature DCs.

This proves that diverse components present in tumor cells, such as melanoma, are useful for the proper execution and performance of this invention.

Figure 9:
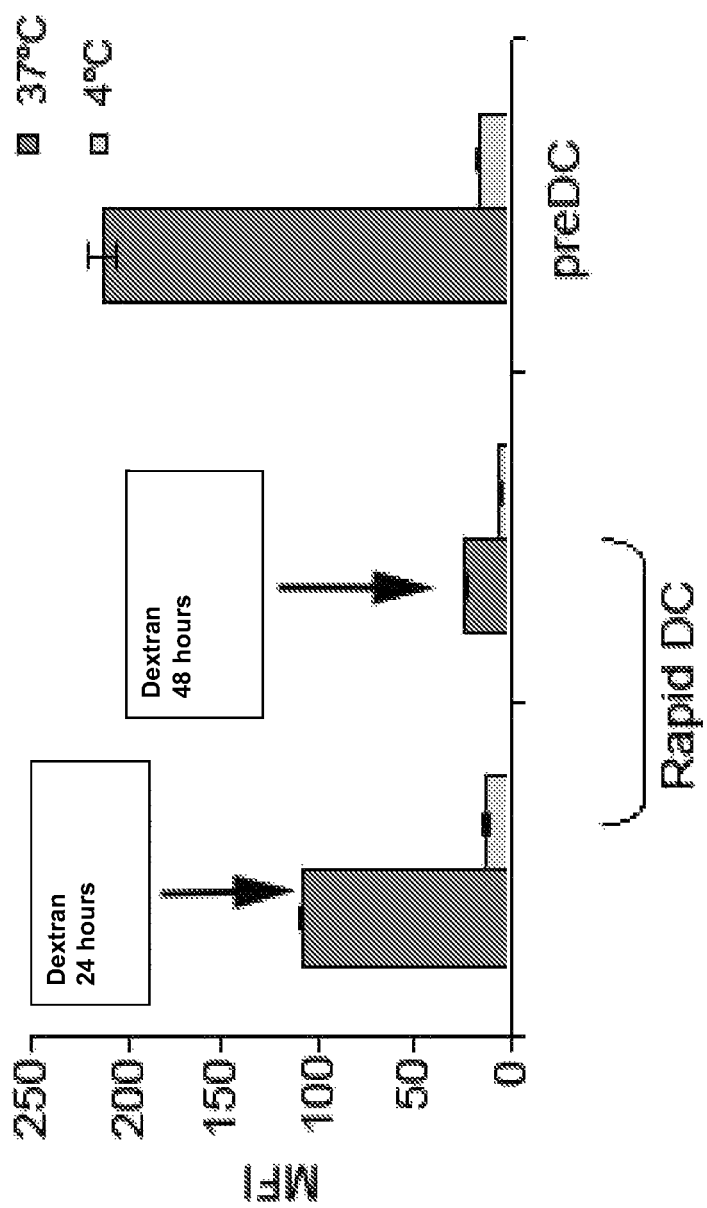

FIG. 9 shows that the Rapid DCs have a low capacity of endocytosis, similar to traditional mature DCs, which is an indication that Rapid DCs are in a final phase of differentiation, that is, optimal for the induction of T lymphocyte activation. A phagocytosis assay was performed with FITC-linked Dextran and the results were measured by flow cytometry. As a control of passive endocytosis cells were kept at 4° C.

Figure 10:
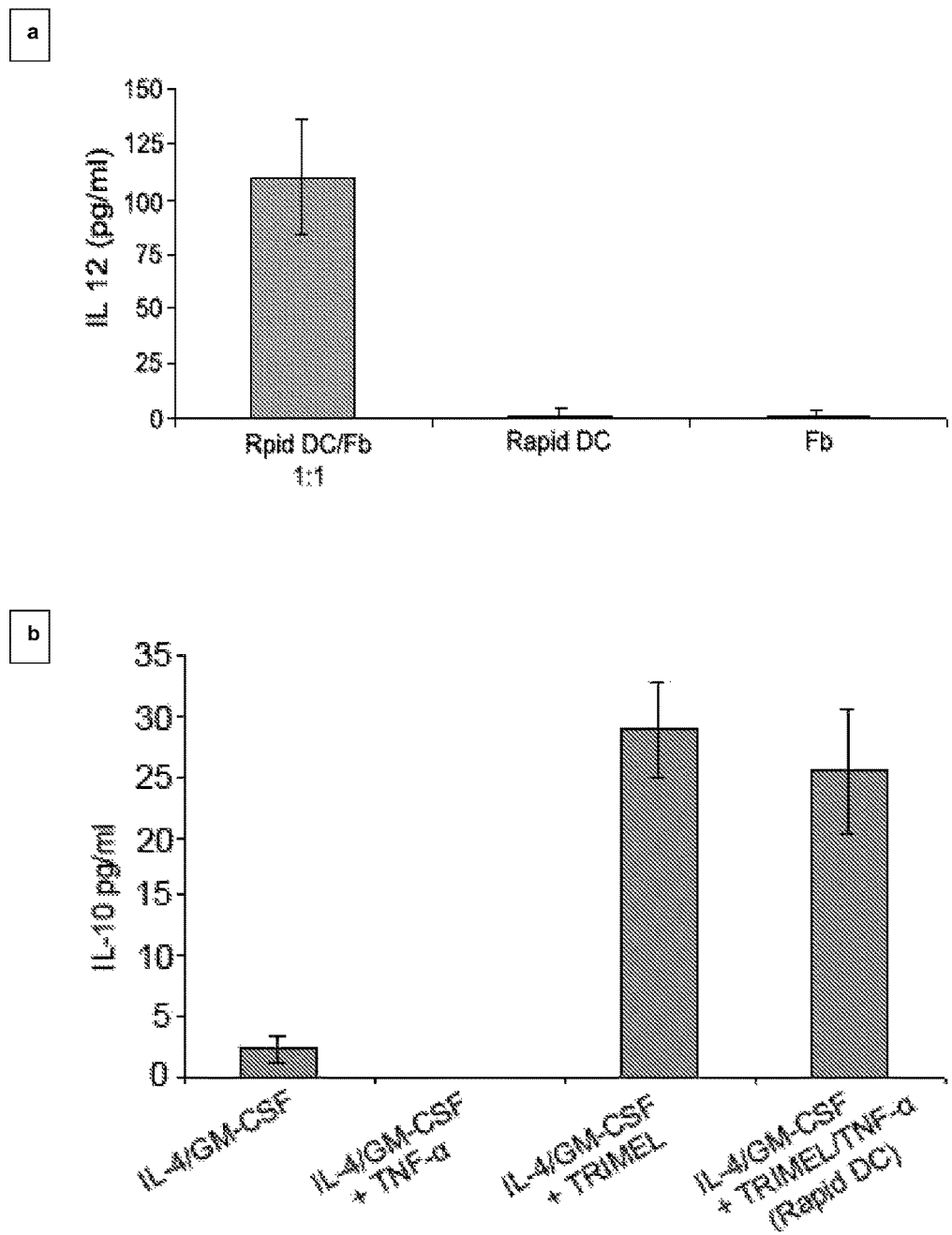

FIG. 10 shows that Rapid DC secretes IL-12 and IL-10 cytokines (a) Different ratios of Rapid DC cells were co-cultured with fibroblasts which express CD40L—constitutively—for 12 hours. An ELISA assay was performed in the supernatant of co-culture to determine the concentration of secreted IL-12 p70. (b) Peripheral blood monocytes were incubated for 24 hours with GM-CSF and IL-4 and then stimulated with TNF-α, TRIMEL or TNF-α and TRIMEL for further 24 hours. An ELISA assay was performed in the culture supernatant to determine the concentration of secreted IL-10. The secretion of these cytokines, especially IL-12, indicates that Rapid DCs are able to induce Th1-type responses, described as very effective against tumors.

Figure 11:
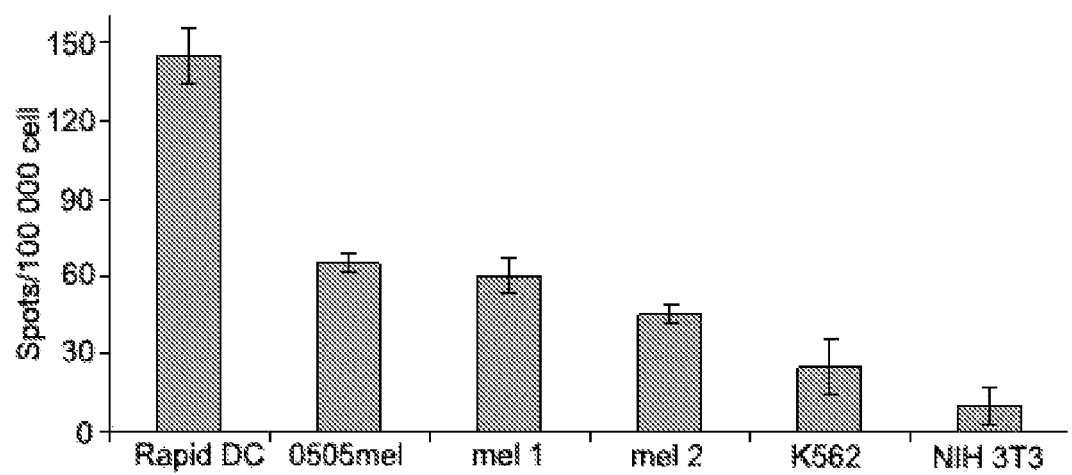

FIG. 11 shows that LTs stimulated with Rapid DC recognize melanoma cells. Autologous PBL were co-cultured for 12 hours with Rapid DC, allogeneic melanoma cells (Mel 1, Mel 2 and 0505 Mel), the NK-sensitive prototype called K562 and rat fibroblast (NIH 3T3). The secretion of IFN-γ was determined by ELISPOT. This result shows that the Rapid DCs are able to stimulate T lymphocytes in vitro with anti-tumor activity.

FIG. 12 shows the results of a Phase I clinical trial using Rapid DC for the treatment of 9 patients with malign advanced melanoma, two patients with pulmonary carcinoma, one with ovarian cancer, one with colorectal carcinoma and one with prostate cancer. None of the patients treated showed important adverse effects, and only in some patients, redness of the injection area and local rash was observed, which provides evidence that the treatment is biologically safe and well tolerated. In addition, 70% of patients develop a type IV delayed hypersensitivity in vivo response (DTH) specific against the tumor antigens, which exceeds the studies published before (Escobar et al. Clin. and Exp. Immunol. 2005) where standard DCs produced immunological response in 50% of patients.

DESCRIPTION OF THE INVENTION

In one hand, this invention refers to an extract of cells and/or tumor tissues with the capacity to induce differentiation and activation of APCs. Another aspect of the invention, in turn, is related to a method to produce DCs ex vivo from peripheral blood monocytes in a shorter time, as compared with the state of the art, where the extract mentioned before is used. DCs produced in this way are useful to make up a therapeutic composition as a vaccine, which is useful in the treatment of cancer and other related diseases.

The method uses common blood cells obtained from patients, donors or blood banks, among other sources, from which mononuclear cells are separated. Then, monocytes are selected and incubated with growth factors and cytokines to be then exposed to a tumor lysate, preferably in the presence of a growth factor. Under these conditions, and in less than three days after the ex vivo cultivation, preferably within 48 hours of ex vivo culture, these cells express markers associated with traditional mature dendritic cells and acquire the capacity of inducing responses from in vitro anti-tumor cytotoxic lymphocytes and generate in vivo immunological responses in patients vaccinated with these cells.

The lysate of tumor cells might be obtained by different means. In one approach to the invention, the lysate of tumor cells contains a mixture of at least two extracts of tumor cells kept under culture. In another approach to the invention, the lysate of tumor cells is obtained from fresh tumor tissue taken from patients with different types of cancer, such as melanoma and uveal melanoma, prostate, kidney, colorectal, gastric, pulmonary, breast, ovarian, testicle carcinomas and other types of neoplasm.

In another approach to the invention, the lysate of tumor cells is obtained from fresh tumor tissue taken from patients with different types of cancer combined with lysate of allogeneic tumor cell lines of the same tumor type.

DETAILED DESCRIPTION OF THE INVENTION

In the context of this invention, a rapid, efficient and cost-effective method has been developed, to allow the training of antigen presenting cells similar to DCs, from monocytes of peripheral blood, so that they may in a short time express surface markers consistent with their function. They are also able to trigger an immune response when they become in contact with the other components of the immune system of an organism.

On one hand, this invention uses cells obtained from blood of patients, donors or blood banks which are separated from the other components of the blood through traditional methods of the art; preferably leukapheresis. In particular leukocytes are selected through the usual methods known in the art, such as density gradient for example. From the fraction of leukocytes, monocytes are separated through traditional methods known by any expert in the art. In a preferred embodiment, the capacity of monocytes to adhere to plastic surfaces is used. In another embodiment, monocytes selection can also be performed by separation kits which use antibodies against the CD14 molecule coupled to magnetic beads for magnetic selection of the desired cellular type.

In a preferred embodiment of the invention, the peripheral blood mononuclear cells are incubated at $13 \times 10^6$ cells per ml, although concentrations between $10^4$ and $10^{10}$, preferably between $10^5$ and $10^7$ are also allowed in a culture medium free from bovine fetal serum. The culture may take place in proper containers, such as different well number plates, bottles, cell reactors and others. Temperatures between 30 and 40° C. are tolerated; preferentially 37° C. in an atmosphere of about 5% $CO_2$ should be used for 1 to 4 hours, with an ideal time of about 2 hours.

Cells that remained attached to the container (well) correspond to monocytes, and are kept under culture in the presence of 100 to 800 U/ml, preferably between 400 and 600 and with an ideal concentration of 500 U/ml of cytokines such as interleukins preferentially IL-4; and in the presence of 500 to 1,100, preferably between 700 and 900 and more preferably as an ideal concentration around 800 U/ml of at least one growth factor, most preferably GM-CFS. The incubation can be extended for at least 10 hours, although incubation times of more than 18 hours are preferred reaching and ideal time of about 22 hours.

Then, the cells can be incubated for at least 10 more hours, ideally 18 hours, and preferentially for about 24 hours. In this second incubation cycle, the cells are kept in culture medium alone or ideally supplemented with a growth factor, like TNF-α, or with the mixture of tumor cells lysate described above or with both components at the same time. In another embodiment of the invention, the mixture of tumor cells lysate described above may be combined with other pro-inflammatory cytokines such as IFN-γ, IL-6, IL-1β or other factors like prostaglandin E2, CpG, thermal shock proteins, Toll-like receptors (TLR) ligands or other factors that activate DCs maturation.

Regarding the use of growth factors, TNF-α might be used at a concentration between 100 pg/ml to 100 ng/ml, ideally between 1 ng/ml to 50 ng/ml, more preferably between 2 ng/ml to 20 ng/ml and ideally around 10 ng/ml.

An integral and essential part of this invention is the mixture of lysate or extracts of tumor cells. This is a mixture made up by at least two cell lines of tumors from metastatic tissue deriving from patients with cancer. In a preferred embodiment of the invention, the tumor cells are selected from malign melanomas and correspond to three cell lines, preferably deriving from gland metastasis. Another alternative provided by the invention, the lysate of tumor cells is obtained from fresh tumor cell derived from patients with different kinds of cancer combined or not with lysate of allogeneic tumor cell lines of the same tumor type. The phenotype of used cells is confirmed through conventional techniques in order to determine the expression of tumor-associated antigens. The cells or tissues are then incubated between 15 minutes and 4 hours, with a preferred timing of 1 and 3 hours ideally around 2 hours at a temperature that range between 39 and 44° C., more preferably between 40 and 43° C. and preferentially near 42° C. in a serum-free culture medium. Later, the cells and/or tissues are placed at physiological temperature again, that is, around 37° C. for 1 to 6 hours, ideally between 2 and 4 hours preferentially 3 hours before being lysate.

Cells treated in this way are subject to 1 to 6 freezing and thawing cycles, preferably 2 to 4 cycles, and ideally 3 cycles are used. For each freezing cycle, the cells are introduced into a tank containing liquid nitrogen, which freezes them instantly and then thawed to 35° to 40° C.

The lysate or extract obtained is subject to homogenization by ultrasound for 30-second 2 to 10 cycles at 30 to 40 KHz in a standard sonicator. Finally, the lysate or extract of each tissue is irradiated at doses ranging between 40 and 120 Gy, preferably between 70 and 90 Gy and preferentially around 80 Gy. Later, the lysate may be mixed or not on equal parts or individually used depending on the type of tumor to be treated. The lysate or extract obtained is used in the culture of dendritic cells at a concentration between 1 µg/ml and 1 mg/ml and ideally around 100 µg/ml.

Figure 3:
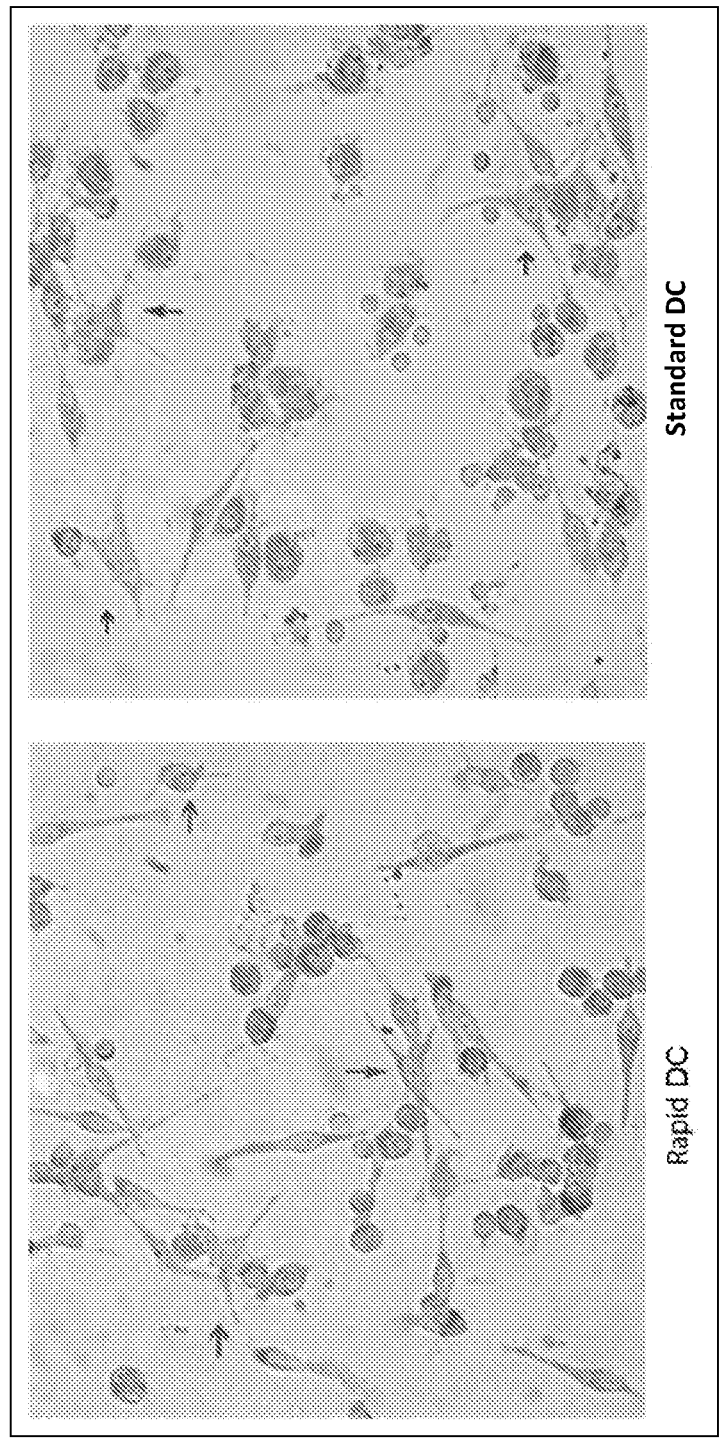
FIG. 3 shows the morphology of rapid differentiation dendritic cells (Rapid DC) belonging to this invention, which does not differ from the morphology of standard DCs (7 days). DCs are identified with arrows.
Figure 4:
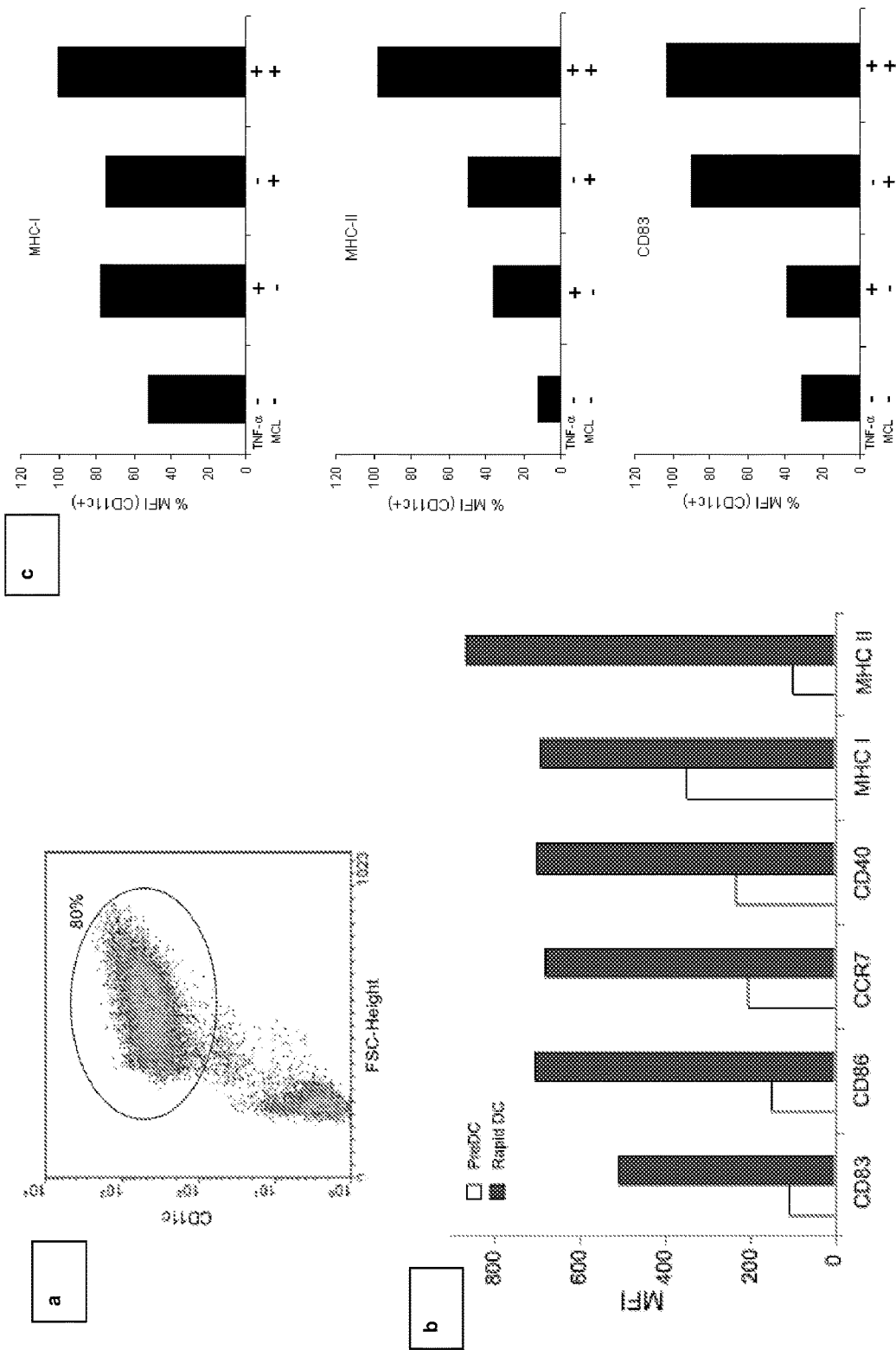
FIG. 4 shows monocytes incubated with GM-CSF and IL-4 and stimulated with a lysate obtained from the mixing of melanoma lines Mel 1, Mel 2 and Mel 3 called TRIMEL and TNF-α. These cells develop the characteristic phenotype of mature DCs within 48 hours (Rapid DC). (a) As described hereinafter in this invention, Rapid DCs were generated and stained with monoclonal antibody (MAb) anti-CD11c (myeloid DCs marker) conjugated with PE to be then read through flow cytometry. The gated population represents the percentage of positive CD11c cells from the total cells obtained after culture (figure is representative staining of 5 different patients). (b) CD11c+ DCs were analyzed for the expression of CD83, CD86, CCR7, CD40, class I MHC and class II MHC. The expression analysis of these markers indicated that Rapid DCs had the characteristic phenotype of mature dendritic cells.
Figure 5:
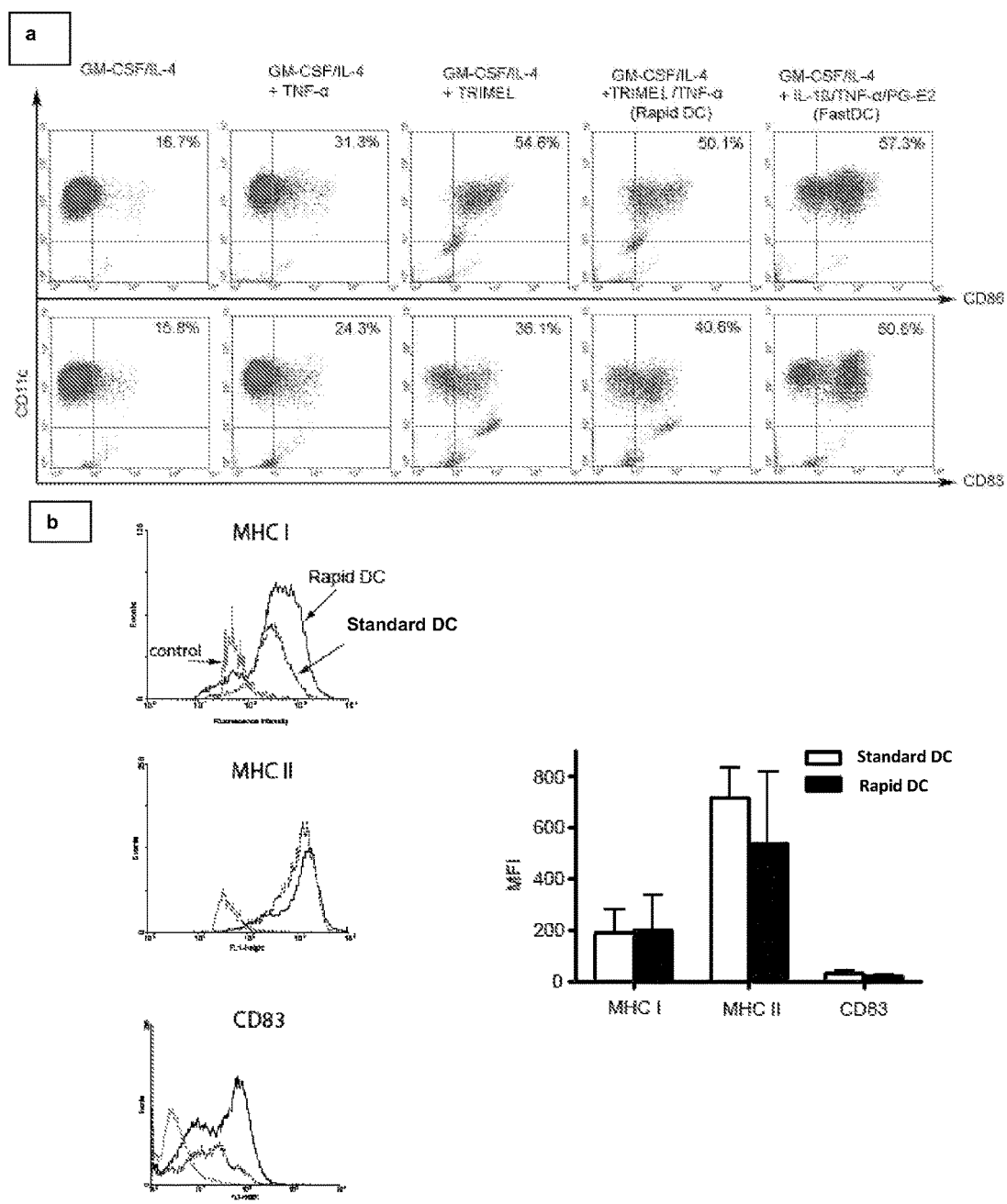
FIG. 5 shows images illustrating that the cells obtained through the Rapid DC method had a similar phenotype to cells obtained by the short FastDC protocol, as well as traditional 7-day DCs. Monocytes incubated with GM-CSF and IL-4 for 24 hours were cultured for additional 24 hours with culture medium alone, TNF-α, TRIMEL alone, TNF-α and tumor lysate TRIMEL or IL-β+IL-6+INF-α+PG-E2 (Fast DC cells). (a) The expression of myeloid DCs markers, CD11c+ and DCs maturation markers, such as CD86 and CD83 was determined by flow cytometry. (b) As described hereinafter in this invention and in the state of the art, Rapid DCs and traditional 7-day DCs were generated and the following markers were determined by flow cytometry: CD11c, class I MHC, class II MHC and CD83. Histograms representative of 2 independent experiments show CD11c+ cell. Bars represent the MFI of positive CD11c cells. These results show that with a shorter method and using fewer factors DCs are obtained with similar characteristics to more complex protocols described in the state of the art.
Figure 6:
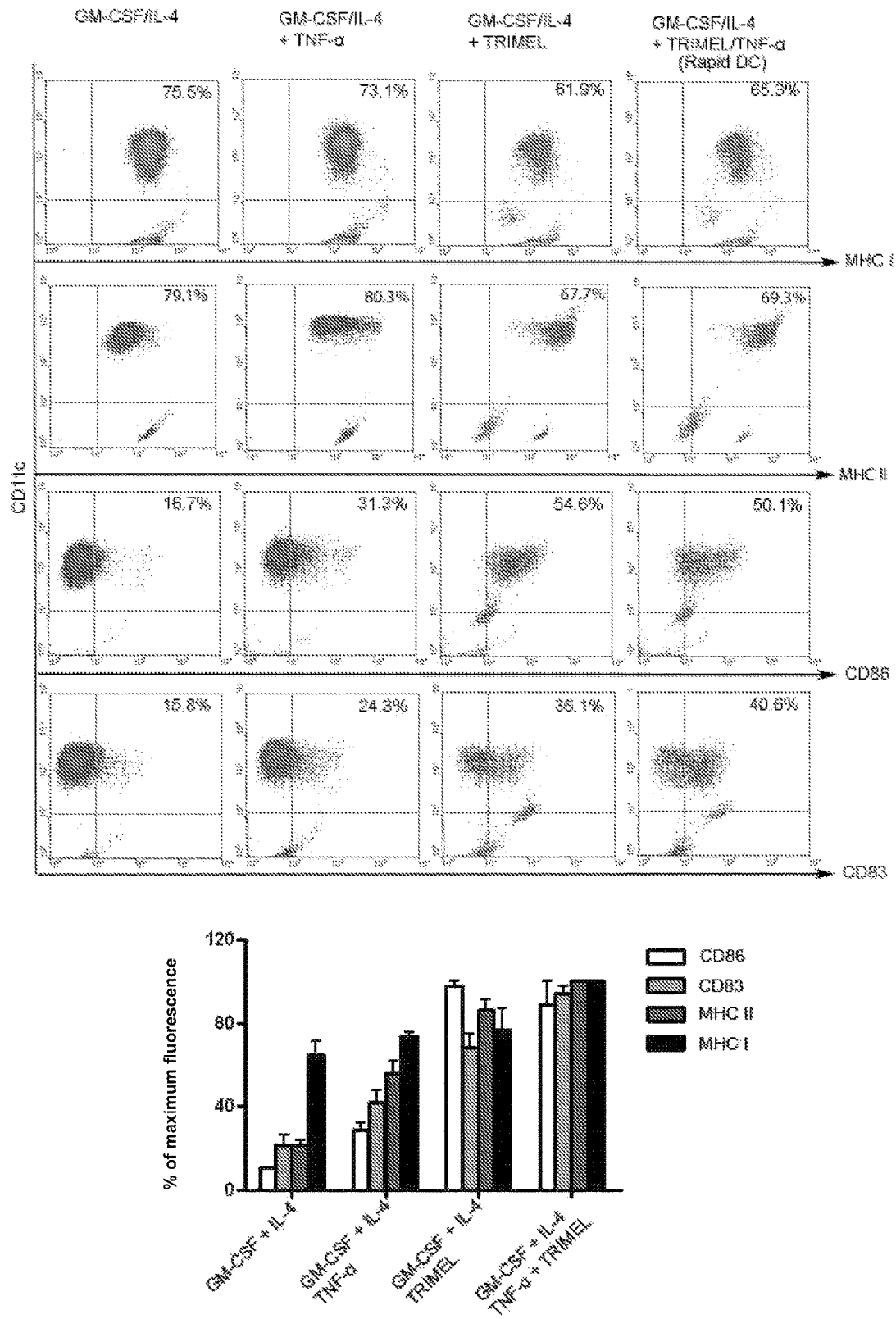
FIG. 6 shows that the combination of melanoma lysate called TRIMEL with TNF-α induces Rapid DC to a powerful maturation process. The evaluation is done by flow cytometry analysis for CD11c, CD86 and CD83 markers of monocytes treated for 24 hours with IL-4 and GM-CSF and without a later stimulus, only stimulated with TRIMEL or TNF-α or with TRIMEL and TNF-α. The bars represent the MFI percentage of positive CD11c cells. This result also indicates that the tumor lysate called TRIMEL is able by itself and without TNF-α to induce the expression of markers associated with mature DCs.

A quite outstanding development of this invention is that the extract of tumor cell lysate described is able to stimulate the differentiation of dendritic cells from preactivated monocytes with differentiation cytokines. This maturation induction and differentiation occurs even in the absence of other cytokines or maturation factors existing in the state of the art. In these cases, it was noted that after hours of treatment with the lysate, monocytes showed a morphology equivalent to DCs classically incubated for 7 days (FIG. 3), which confirms the advantages of the method proposed and the prominent qualities of the extract developed. Also, the monocytes activated with tumor cells extracts showed the CD11c membrane marker expression, which is characteristic of the myeloid-type DCs in addition to the expression of a number of membrane markers characteristic of mature DCs, such as MHC I and MHC II, CD83, CD86, CD40 and CCR7 (FIGS. 4 to 6).

Figure 7:
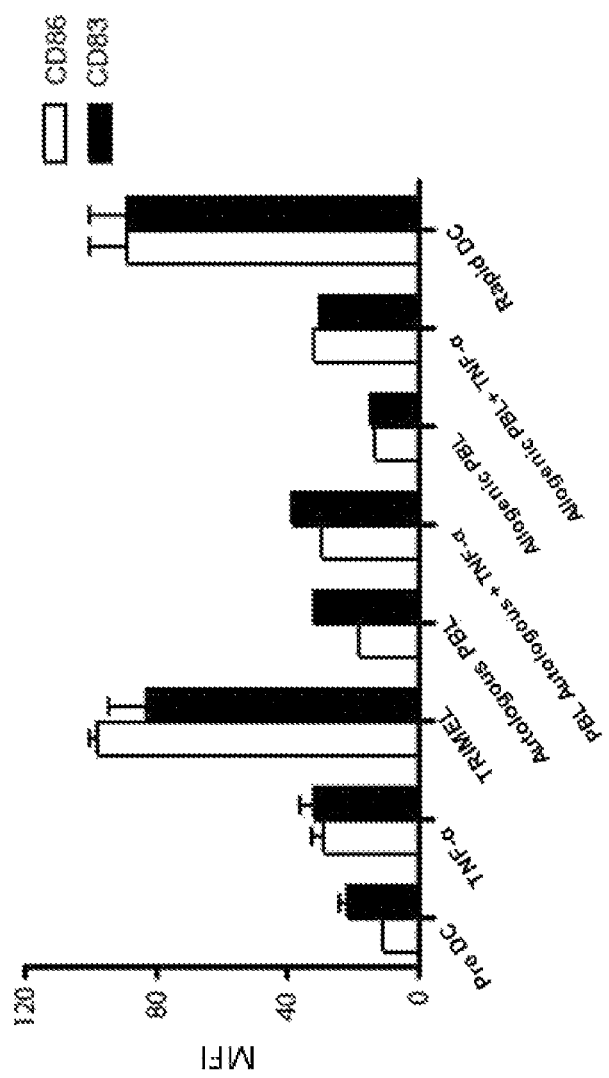
FIG. 7 shows that lysate from normal cells are not able to induce Rapid DC maturation. Lysate were prepared from autologous and allogeneic PBL and they were used to stimulate the Rapid DCs. The expression of CD11c, CD86 and CD83 markers was measured by flow cytometry. The bars represent the fluorescence percentage as regards the maximum fluorescence of positive Colic cells. (PBL: peripheral blood lymphocytes). This result indicates that monocytes maturation process depends of factors that are present in the tumor lysate and not in normal cells.

Of pivotal importance is that most tumor lysate and not lysate from normal cells are able to induce this differentiation and maturation, which is a property that has not been described for tumor cells (FIG. 7). A key feature of this invention is indeed related to the role played by the components of tumor cells in the differentiation of monocytes to DCs and their later maturation. There is indeed some background information in the state of the art on the capacity of some necrotic tumor cells of inducing DC maturation (Bhardwaj N. et al 2000, J Exp Med. 191:411-6; Escobar et al. 2005, Clin. Exp. Immunol. 142:555-68), but there is no evidence regarding the effect of these cells and their components in inducing also differentiation of monocytes to DCs. In this invention, it is described that tumor lysate and/or a mixture of them are able to act on monocytes inducing the differentiation thereof to professional antigen-presenting cells, similar to DCs and giving them the capacity of activating the T lymphocyte-mediated immune response against tumor cells, thus having a great therapeutic potential.

Another aspect of the invention refers to the pharmaceutical composition or vaccine obtained with DCs produced under the methods described above. This invention provides evidence that DCs obtained under the method hereby invented; corresponding to rapid differentiation DCs has the power of inducing potent immune anti-tumor responses. This quality is reflected in the fact that T lymphocytes co-cultured with rapid DCs are able to produce inflammatory cytokines such as interferon-γ and TNF-α and recognize and destroy lines of allogeneic melanomas through cytolysis (FIG. 11). Also the cells obtained through the method described herein are able of inducing the proliferation of specific T lymphocytes against tumor cells.

Another fundamental outcome of the invention corresponds to the use of dendritic cells obtained under method of the invention in patients with melanoma, other kinds of cancer or another type of immune response-associated diseases (FIG. 12).

Example 1

The method of this invention allows obtaining DCs that may be incorporated to vaccines to treat individuals suffering from different kinds of cancer. To this effect, in order to treat patients suffering from these diseases, blood is obtained through a standard method to obtain blood by-products called leukapheresis. A volume equal to 2 blood volemia is obtained from each patient. Blood is processed in a biohazard laboratory. The leukapheresis product is diluted in PBS in a 1:1 dilution. Then, this product is separated by a density gradient called Lymphoprep™ as described in the state of the art. The white fraction of blood consisting in the peripheral blood mononuclear cells (PBMC) is washed three times with PBS and then placed in culture bottles (Nunc T75) at a concentration that ranges between 10 and $40 \times 10^6$ of PBMC/ml of a serum-free culture medium, concentrations between 20 and $30 \times 10^6$ of PBMC/ml of a medium are used and ideally $25 \times 10^6$ of PBMC/ml of a medium (serum free). In another protocol allowed within the parameters of the invention, the PBMCs are cultivated in cell reactors or in roller-type bottles or cultivation bags, keeping the concentration indicated above. The cultivation is supplemented with cytokines such as IL-4 and GM-CSF as already described. Twenty-two hours after cultivation, the maturation factors are added, which correspond to tumor lysate alone or in presence of cytokines and/or differentiation factors, preferably TNF-α as already described. After further 24 hours of incubation and about 48 hours after culture start, DCs are harvested, washed and frozen in 1 ml of freezing medium in cryovials at doses between 1 and $50 \times 10^6$ of DCs, preferably between 20 and $30 \times 10^6$ in 500 μl of freezing medium. The freezing medium consists in 90% de-supplemented autologous plasma treated at 56° C. for inactivation of complement for 20 minutes and 10% dimethylsulfoxide (DMSO). Vials are then frozen using isopropanol freezing chambers and kept in liquid nitrogen. For vaccination, the vial is thawed at 37° C. and mixed with 150 μl of KLH adjuvant (hemocyanin deriving from the Keyhole limpet mollusk) at a concentration of 1 μg/ml and intradermally injected into one of the patient's limbs. This process can be repeated between 2 and 10 times, preferably between 3 and 5 times and ideally 4 times, at 7 to 30 day intervals, preferably 10 days. Each immune therapy consists in 4 immunization cycles that may be repeated every 6 months or every year according to the decision of the attending physician. Most patients immunized under this method show the presence of specific T lymphocytes against tumors detected through cytokine secretion assays and develop after immunization a delayed hypersensitivity reactions type IV in the skin against tumor lysate, which shows the memory immunological response against tumor cells.

Example 2

The production process of the antigen presenting cells called Rapid DC is described above. The method is rapid, efficient and cost-effective, thus allowing training antigen presenting cells similar to DCs from peripheral blood monocytes, so that in a short time they may express surface markers according to their function and are able to trigger an immune response.

Under this method, leukocytes are obtained from the blood through leukapheresis. These cells are separated through density gradient using Lymphoprep™ in order to eliminate red cells excess. From the fraction of leukocytes, monocytes are separated using their characteristic capacity of adhering to plastic.

Then peripheral blood mononuclear cells are incubated at a concentration of $13 \times 10^6$ of cells by ml, in a culture medium free from bovine fetal serum called AIM-V (Life Technologies, USA). Culture is done in wells at 37° C. in an atmosphere of about 5% $CO_2$ for 2 hours.

The cells remaining adhered to the well correspond to monocytes, and are kept under culture in the presence of 500 U/ml of IL-4; and 800 U/ml of GM-CFS. The cells remain under the above mentioned culture conditions for about 22 hours.

Then, the cells are incubated for at least further 24 hours. In this second incubation cycle, the cells are kept in a medium supplemented with 10 ng/ml of TNF-α, and with the mixture of tumor cells lysate as described in this invention.

After 48 hours of culture start, the cells obtained are separated. Their morphology is equivalent to that of DCs cells obtained through other methods. These cells are washed and frozen for their use afterwards.

Example 3

Under this invention, it has been described that a mixture of lysate or extracts of tumor cells may be used in this invention in order to induce DCs. This mixture is manufactured from three melanoma cell lines obtained from metastatic tissue from patients with malign melanoma, which will be called TRIMEL. The cells used are checked through conventional techniques in order to determine the expression of melanoma-associated antigens. Cells or tissues are then incubated for 2 hours at a temperature of 42° C. in a serum-free culture medium. Later, the cells and/or tissues are placed at physiological temperature again, at near 37° C. for 3 hours before being lysate.

The cells treated in this way are subject to 3 cycles of freezing and thawing. For each freezing cycle, cells are introduced to a tank containing liquid nitrogen, being instantly frozen and they are then thawed at 37° C.

The lysate or extract obtained is subject to a homogenization of 4 cycles of 30-second ultrasound (40 to 40 KHz) in a standard sonicator. Finally the lysate or extract of each tissue is irradiated to 80 Gy doses. Lysate are mixed in equal parts and used for the in vitro activation of monocytes of patients with melanoma. The lysate or extract obtained may be used for the culture of dendritic cells.

Example 4

In subjects with prostate and colon cancer, an APC production protocol similar to the one described above is used. The melanoma lysate is replaced with another one made up by two lines of prostate carcinoma and a lysate of autologous prostate tissue or cell lines and tissue of colon carcinoma. Following the same vaccination scheme as described above, a DTH response was induced against the prostate and colon tumor lysate. In clinical evaluations, a reduction of the PSA prostate antigen levels was noted after treatment. Considering that the levels of plasmatic PSA always correlate with the progress of disease, these results indicate that the procedure performed in this invention allows obtaining high quality and efficient DCs for immune therapy. It also provides evidence that mixing lysate or extracts of tumor cells, as well as their obtaining process under this invention, are useful for obtaining DCs.

The invention claimed is:
1. An in-vitro method to obtain activated antigen-presenting cells (APCs) that are dendritic cells (DCs), and that are useful in the preparation of vaccines for the treatment of cancer, the method comprising:
   a) obtaining monocytes from peripheral blood cells (PBMC);
   b) pre-activating monocytes obtained from step a) together with granulocyte macrophage colony stimulating factor (GM-CSF) and interleukin-4 (IL-4) for at least 10 hours;
   c) incubating activated monocytes obtained from step b) for an additional 24 hours with a lysate obtained from three melanoma cell lines wherein the three melanoma cell lines are Mel 1 (IDAC accession number 260916-01), Mel 2 (IDAC accession number 260916-02), and Mel 3 (IDAC accession number 260916-03) and the three melanoma cell lines have been thermally pre-treated, occurring in a single step, differentiation, maturation and loading of DCs; and d) harvesting and washing the APCs obtained in step c), wherein, in step c), thermally pre-treating comprises incubation of the melanoma cell lines at a temperature between 39-44° C. for 15 minutes to 4 hours in a serum-free culture medium, and said thermally pre-treating is followed by incubation of said melanoma cell lines at 37° C. for 1 to 6 hours.

2. The method of claim 1, wherein said temperature of thermal pre-treatment is between 40 and 43° C.

3. The method of claim 2, wherein said temperature of thermal pre-treatment is 42° C.

4. The method of claim 1, wherein thermal pre-treatment is for between 1 to 3 hours.

5. The method of claim 4, wherein thermal pre-treatment is for 2 hours.

6. The method of claim 1, wherein the thermally pre-treated melanoma cell lines have been incubated at a temperature between 39 and 44° C., and then have been incubated at 37° C. from 2 to 4 hours.

7. The method of claim 6, wherein incubation at 37° C. is for 3 hours.

8. The method of claim 1, wherein, in step b), said monocytes are provided as PBMC, which are incubated with GM-CSF and said IL-4 at a concentration of $10\text{-}40\times10^6$ cells/ml in serum-free culture medium.

9. The method of claim 8, wherein said concentration is between $20\text{-}30\times10^6$ cells/ml.

10. The method of claim 9, wherein said concentration is $25\times10^6$ cells/ml.

11. The method of claim 1, wherein, in step b), a concentration of said IL-4 is between 100-800 U/ml.

12. The method of claim 11, wherein said concentration is between 400-600 U/ml.

13. The method of claim 12, wherein said concentration is 500 U/ml.

14. The method of claim 1, wherein, in step b), a concentration of said GM-CSF is between 500-1100 U/ml.

15. The method of claim 14, wherein said concentration is between 700-900 U/ml.

16. The method of claim 15, wherein said concentration is 800 U/ml.

17. The method of claim 1 wherein step c) further comprises incubating said monocytes with one or more pro-inflammatory factors selected from IFN-.gamma., IL-6, IL-1.Beta, prostaglandin E2, CpG, heat shock proteins, ligands of Toll-like receptors (TLR) and mixtures thereof.

18. The method of claim 1, wherein, in step c), a concentration of TNF-alpha is between 100 pg/ml-100 ng/ml.

19. The method of claim 18, wherein said concentration is between 1 ng/ml-50 ng/ml.

20. The method of claim 19, wherein said concentration is between 2 ng/ml-20 ng/ml.

21. The method of claim 20, wherein said concentration is 10 ng/ml.

22. The method of claim 1, wherein a concentration of said lysate is between 1 μg/ml to 10 mg/ml.

23. The method of claim 22, wherein said concentration of said lysate is between 10 μg/ml and 1 mg/ml.

24. The method of claim 23, wherein said concentration of said lysate is 100 pg/ml.

25. The method of claim 1, wherein, in step b), concentrations of IL-4 and GM-CSF are 500 U/ml and 800 U/ml, respectively.

26. The method of claim 1, wherein said method further comprises step e) freezing APCs from step d).

* * * * *